(12) United States Patent
Bez (10) Patent No.: US 11,519,873 B2
(45) Date of Patent: Dec. 6, 2022

(54) CALIBRATION OF A HUMIDITY SENSOR DEVICE

(71) Applicant: MEAS France SAS, Toulouse (FR)

(72) Inventor: Denis Bez, Le Mouliat (FR)

(73) Assignee: MEAS FRANCE SAS, Toulouse (FR)

( * ) Notice: Subject to any disclaimer, the term of this patent is extended or adjusted under 35 U.S.C. 154(b) by 491 days.

(21) Appl. No.: 16/677,502

(22) Filed: Nov. 7, 2019

(65) Prior Publication Data

US 2020/0150072 A1 May 14, 2020

(30) Foreign Application Priority Data

Nov. 14, 2018 (EP) ........................................ 8306487

(51) Int. Cl.
*G01N 27/22* (2006.01)
*G01N 25/56* (2006.01)
*G01N 33/00* (2006.01)

(52) U.S. Cl.
CPC ........... *G01N 27/223* (2013.01); *G01N 25/56* (2013.01); *G01N 33/0006* (2013.01)

(58) Field of Classification Search
CPC .... G01N 27/223; G01N 27/228; G01N 27/22; G01N 25/56; G01N 25/66; G01N 33/0006; G01N 27/048
See application file for complete search history.

(56) References Cited

U.S. PATENT DOCUMENTS

2005/0253912 A1* 11/2005 Smith ................. B41J 29/02
347/102

FOREIGN PATENT DOCUMENTS

CN 103091366 A 5/2013
FR 2716975 A1 9/1995

OTHER PUBLICATIONS

Extended European Search Report, European Application No. 18306487. 2-1001, European Filing Date, May 14, 2019.

* cited by examiner

*Primary Examiner* — Lee E Rodak
(74) *Attorney, Agent, or Firm* — Snell & Wilmer L.L.P.

(57) ABSTRACT

The present invention relates to a method of calibrating a humidity sensor device, comprising the steps determining a first dew point and a first relative humidity at a first temperature in an environment by the humidity sensor device using a first calibration offset; subsequently heating the humidity sensor device, in particular, by self-heating, thereby heating the environment to a second temperature higher than the first temperature; subsequently determining a second dew point at the second temperature by the humidity sensor device; subsequently determining whether the determined second dew point differs from the determined first dew point by more than a predetermined difference; and subsequently changing the first calibration offset of the humidity sensor device by a predetermined value to obtain a second calibration offset, if it is determined that the determined second dew point differs from the determined first dew point by more than the predetermined difference.

13 Claims, 5 Drawing Sheets

CALIBRATION OF A HUMIDITY SENSOR DEVICE

CROSS-REFERENCE TO RELATED APPLICATIONS

This patent application claims the benefit of European Patent Application No. 18306487.2 filed on Nov. 14, 2018, which patent application is hereby incorporated by reference in its entirety.

FIELD

The present invention relates to a humidity sensor device and, in particular, to the calibration of a humidity sensor device configured for measuring a relative humidity and determining a dew point in an environment.

BACKGROUND

Humidity can be measured by a number of techniques based on a resistance change and a capacitance change of a suitable material. In a semiconductor-based system for determining a relative humidity (ratio of the partial pressure of water vapor to the saturation vapor pressure of water at a given temperature) by means of measuring a capacitance, for example, humidity can be measured based on the reversible water absorption characteristics of polymeric materials serving as a capacitor dielectric.

A conventional capacitive relative humidity sensor device, in general, includes a semiconductor substrate, and a pair of electrodes, which are formed on a surface of the semiconductor substrate and face each other across a particular distance. A humidity-sensitive dielectric film is placed between the electrodes and formed on a surface of the semiconductor substrate. The capacitance of the film changes in response to humidity. The sensor detects humidity by detecting changes in capacitance between the pair of electrodes in response to variations in the surrounding humidity. Humidity sensing elements of the capacitance sensing type usually include a moisture-insensitive, non-conducting structure with appropriate electrode elements mounted or deposited on the structure, along with a layer or coating of a dielectric, highly moisture-sensitive material overlaying the electrodes and positioned so as to be capable of absorbing water from the surrounding atmosphere and attaining equilibrium in a short period of time.

The response offset and slope for the integrated relative humidity sensor device can be set to particular values in order to achieve a desired value of accuracy for the sensor. The accumulated charges of the capacitor element can be read out by means of an appropriate conditioning circuit that outputs a DC voltage or change is oscillation frequency of an oscillator that can be detected responsive to the accumulation of charges in the dielectric layer and represent measures of the capacitance and, thereby, a relative humidity. Based on the relative humidity and a detected temperature the absolute humidity and dew point can be determined. Thus, a dew point at a windscreen of a vehicle can be determined by means of a humidity sensor device, for example.

Measuring the relative humidity by a sensing capacitor demands for calibrating a measurement circuitry, in particular, adjusting the offset, in order to interpret the changing physical characteristics of the sensing capacitor in terms of the relative humidity. Climatic chambers for precise calibration are known that, for example, make use of saturated or non-saturated solutions of salts. However, long stabilization times and involved communication with test benches are needed. Time and, thus, money, spent for calibration is significant.

Moreover, a sensing capacitor and measurement circuitry may be realized on an integrated circuit chip, for example, in the context of CMOS technology, and calibrated at the time of manufacture. A wafer having many IC chips may be manufactured at one time while the actual electronic devices containing the manufactured IC chips are assembled and calibrated at a later time and often at a different facility. Thus, individually calibrating each electronic device at the time of assembly becomes time and labor consuming.

In view of the above, a problem underlying the present invention is to provide for an efficient and reliable procedure of calibrating a relative humidity sensor device means.

SUMMARY

The present invention addresses the above-mentioned problems by providing a method of calibrating a (relative) humidity sensor device according to claim 1. The method comprises the subsequently (in the cited order) performed steps of:
  a) determining a first dew point and a first relative humidity at a first temperature in an environment by the humidity sensor device using a first calibration offset;
  b) heating the humidity sensor device, in particular, by self-heating, thereby heating the environment (locally) to a second temperature higher than the first temperature;
  c) determining a second dew point at the second temperature by the humidity sensor device;
  d) determining whether the determined second dew point differs from the determined first dew point by more than a predetermined difference (tolerance); and
  e) changing the first calibration offset of the humidity sensor device by a predetermined value (for example, by some predetermined fraction of the first calibration offset) to obtain a second calibration offset, if it is determined that the determined second dew point differs from the determined first dew point by more than the predetermined difference.

The method makes use of heating of the humidity sensor device, in particular, self-heating of the humidity sensor device. In the art, self-heating (heat caused by operation) is considered a severe problem that has to be overcome by appropriate calibration. Contrary, according to the present invention the phenomenon of self-heating can be used for the calibration process. The self-heating may be caused by a processing means, for example, a microcontroller, of the humidity sensor device. It is noted, however, that the disclosed procedure does also work (additionally or alternatively) with some external heating of the humidity sensor device.

The disclosed procedure makes use of the fact that in a stable environment/closed air volume an increase of the temperature results in a decrease of the relative humidity such that the dew point (temperature) maintains constant. Any deviation from the constant value of the dew point results from some de-calibration or calibration error. Thus, self-calibration (auto-calibration) can be achieved in a very reliable and cost and time saving manner by adjusting a calibration offset based on determined differences between a dew point determined after a controlled heating of the sensor and a dew point initially determined before that heating. The calibration offset is related to a relative humidity that is detected by the humidity sensor device (see also detailed description below). The correct offset allows for correctly translating a measured voltage, for example, to a real relative humidity that is present in the environment.

In particular, according to an embodiment, the first calibration offset is increased by the predetermined value, if it is determined that the second dew point is lower than the determined first dew point and the first calibration offset is decreased by the predetermined value, if it is determined that the second dew point is higher than the determined first dew point.

The inventive method of calibrating a humidity sensor device may include the additional subsequently performed steps of:

f) determining a new value of the first dew point based on the changed calibration offset;
g) subsequently determining a third dew point at a third temperature by the humidity sensor device;
h) subsequently determining whether the determined third dew point differs from the determined new value of the first dew point by more than a predetermined difference; and
i) subsequently changing the calibration offset of the humidity sensor device by the predetermined value, if it is determined that the determined third dew point differs from the determined new value of the first dew point by more than the predetermined difference.

The steps f) to i) may be repeatedly performed until the predetermined difference is no longer reached. Steps f) to i) may be repeated until the respectively determined new (third, fourth, fifth, etc.) dew point (determined at a respective third, fourth, fifth, etc., temperature) differs from the respectively determined new value of the first dew point by not more than the predetermined difference. Thus, accurate calibration can be achieved by an iteration procedure.

Steps a) to e) or steps a) to i) (including repetition until the predetermined difference is no longer reached) may be performed on a periodical basis, for example, with a time period of some hours or minutes, in order to achieve an auto-re-calibration of the humidity sensor device during service time.

According to particular embodiments the third temperature differs from the second temperature by less than 10% of the second temperature and/or the predetermined difference between the determined second dew point and the determined first dew point as well as the determined third dew point and the determined new value of the first dew point is in the range of 0.05° C. to 0.5° C. For example, a predetermined difference (tolerance) of 0.1° C. can be suitably chosen.

At least the steps a) to e) of the inventive method may be performed automatically at a predetermined time period, in particular, between 10 and 2 times an hour. Steps a) to i) may be performed automatically at a predetermined time period and may be repeated until the determined difference in dew point does no longer exceed or match the predetermined difference.

According to a further embodiment, the first dew point, the determined first relative humidity, and the first temperature may be stored, in particular, in a memory of the humidity sensor device in order to be used for the calibration procedure.

Furthermore, it is provided a computer program product comprising one or more computer readable media having computer-executable instructions for performing the steps of the method according to one of the above-described embodiments. Further, it is provided a (relative) humidity sensor device, comprising a memory for storing that computer program product and a processor means configured to run that computer program product. The humidity sensor device can be adapted to be used in automotive applications, for example, for detecting relative humidity and/or a dew point at a windscreen of an automobile.

Additional features and advantages of the present invention will be described with reference to the drawings. In the description, reference is made to the accompanying figures that are meant to illustrate preferred embodiments of the invention. It is understood that such embodiments do not represent the full scope of the invention.

DETAILED DESCRIPTION

The present invention provides a method of (self-)calibrating a (relative) humidity sensor device based on heating of the humidity sensor device. The heating may be a self-heating of the humidity sensor device that occurs during operation of the same, for example, due to a self-heating of at least one of circuitry, a processing means, microcontroller, etc. In a closed environment (for example, regarded as a canonical ensemble) the heating of the humidity sensor device results (at least locally at the location of the measurement) in an increase of the temperature of the environment. Data processing is performed by a processing means of the humidity sensor device.

Figure 1:
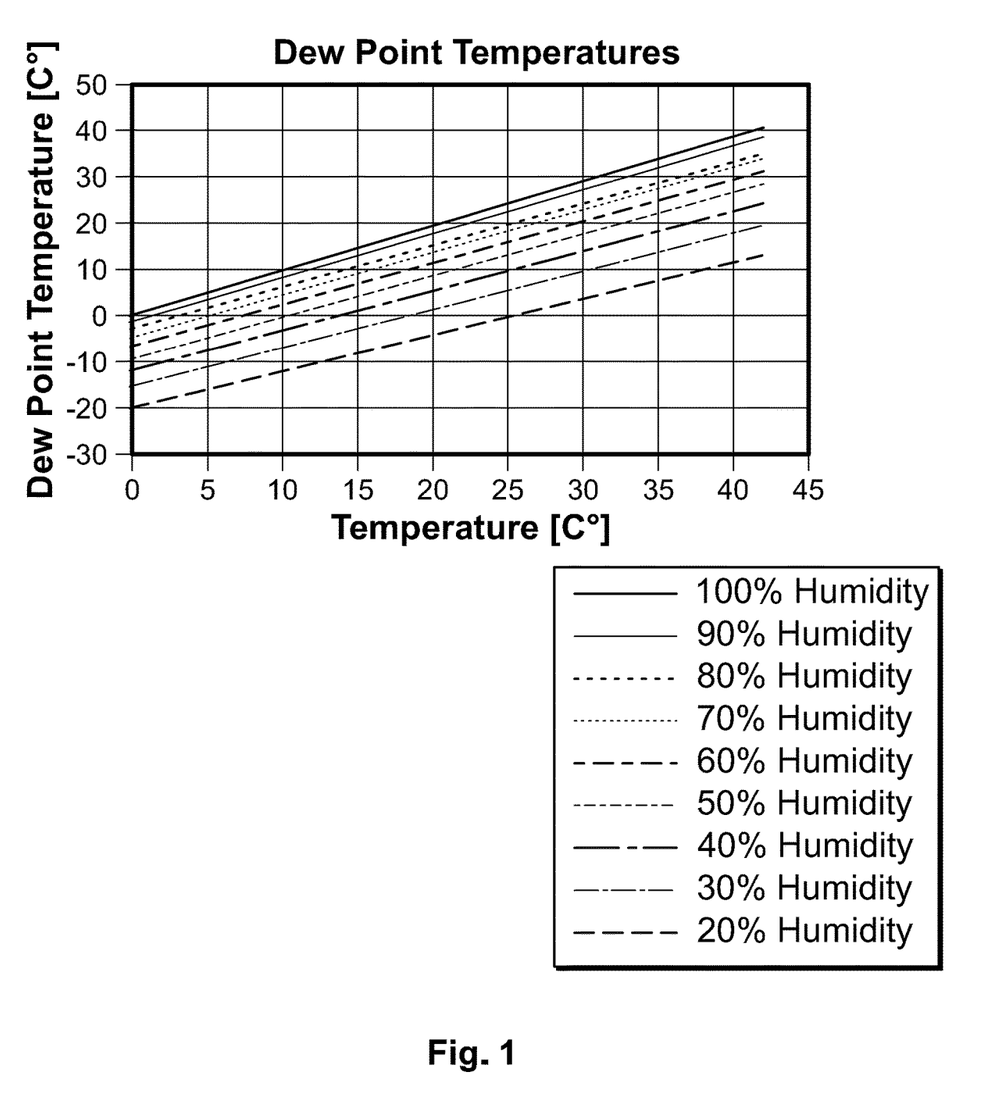
FIG. 1 illustrates the dependency of the dew point on the temperature in a closed environment.

FIG. 1 illustrates the dependency of a dew point on the temperature and relative humidity in a closed environment. The straight lines (with constant slopes) are plotted for different relative humidity values. The dew point i is given by the below-provided equation.

$$\tau(\varphi, T) = K3 \cdot \frac{\frac{K2 \cdot T}{K3 + T} + \ln\varphi}{\frac{K2 \cdot K3}{K3 + T} - \ln\varphi}$$

Wherein T and $\varphi$ denote the temperature and relative humidity, i.e., the ratio of the partial pressure of vapor and the saturation vapor pressure, and K2 and K3 are constants of the Magnus formula, i.e., K3=243.12° C. and K2=17.62° C. for temperatures in the range of −45° C. and 60° C.

In a closed environment an increase in temperature results in a decrease in relative humidity such that the dew point maintains (at least approximately) constant. Thus, if some heating of the humidity sensor device results in a variation of the dew point determined based on the measured relative humidity, the humidity sensor device is not accurately calibrated. In other words, if the relative humidity calibration offset (relating a value of a measured voltage, for example, to a relative humidity value) is wrongly adjusted, the determined dew point will not be constant at varying temperatures (that result in accordingly varying levels of the relative humidity).

After a humidity sensor device has been manufactured a conditioning circuit has to be calibrated. In the case of a resistive or capacitive humidity sensor device a resistivity or capacity changes with changing humidity in an environment wherein the humidity sensor device is to be operated. For example, in a capacitive humidity sensor device, some voltage or charging time is output and has to be translated to the correct relative humidity by an appropriate offset. In the following, a calibration procedure for determining the appropriate offset according to an embodiment of the present invention will be described with reference to FIG. 2.

Figure 2:
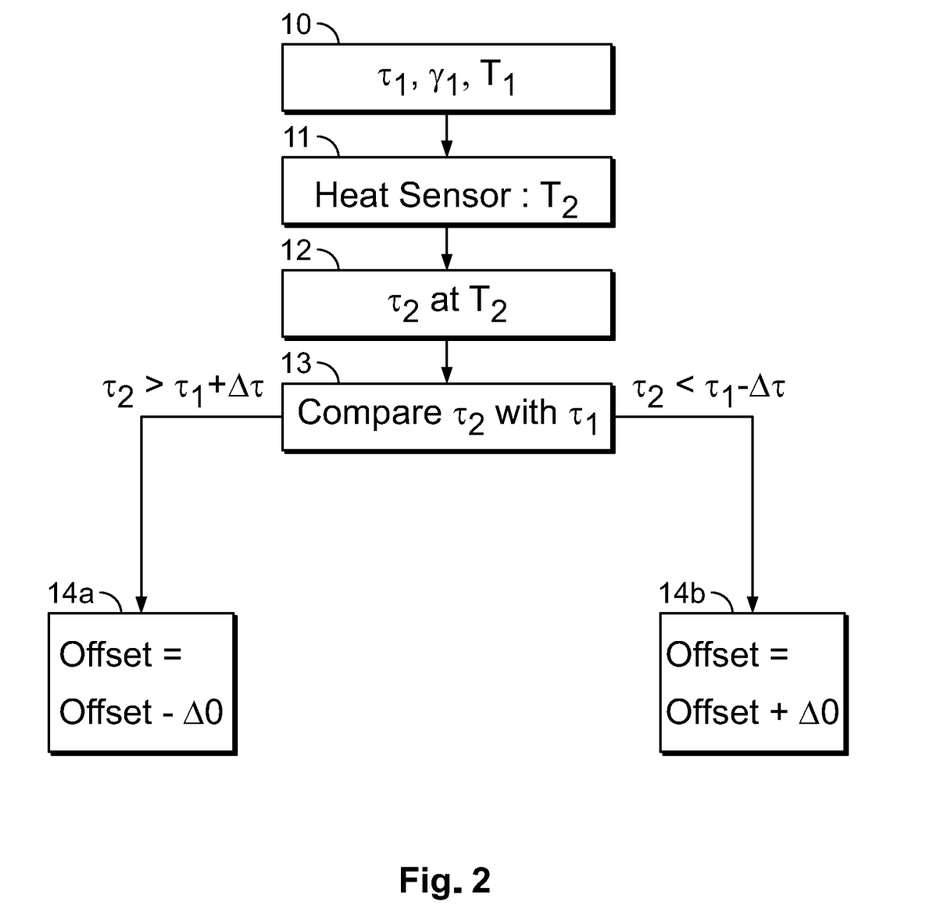
FIG. 2 represents a flow chart illustrating a calibration process according to an embodiment of the present invention.

In a start-up phase, a dew point $\tau_1$ and a relative humidity value $\varphi_1$ are determined 10 by a humidity sensor device based on an initial calibration offset for the measured relative humidity. The humidity sensor device operates in a closed air volume at a given temperature $T_1$ with some first calibration offset. All determined values (including the temperature $T_1$ that might also be detected by the humidity sensor device) can be stored, for example, in a memory of the humidity sensor device.

Next, the humidity sensor device is heated 11 either by some external means, a heater provided in the humidity sensor device or by self-heating of the humidity sensor device caused by operation of the same. For example, operation of some circuitry, in particular, some data processing means, of the humidity sensor device may cause the self-heating.

After some time period of heating and/or after some particular temperature of the humidity sensor device and, thereby, the local environment of the same, has been reached the dew point $\tau_2$ is determined 12 by the humidity sensor device for a second time at a second temperature $T_2$. The second dew point $\tau_2$ determined at the temperature $T_2$ is compared 13 with the first dew point $\tau_1$ determined at the temperature $T_1$ before.

If the comparison 13 shows that the determined second dew point $\tau_2$ exceeds the determined first dew point $\tau_1$ by more than a predetermined (tolerance) range $\Delta\tau$, $\tau_2 > \tau_1 + \Delta\tau$, it is determined that the offset value is too high, i.e., the relative humidity is overestimated, and, consequently, the first calibration offset for the measured relative humidity is reduced 14a by some predetermined value $\Delta O$, for example, some percentage of the first calibration offset, for example, 0.05 to 0.2% of the first calibration offset.

If, on the other hand, the comparison 13 shows that the determined second dew point $\tau_2$ falls below the determined first dew point $\tau_1$ by more than a predetermined range $\Delta\tau$, $\tau_2 < \tau_1 - \Delta\tau$, it is determined that the offset value is too low, i.e., the relative humidity is under-estimated, and, consequently, the first calibration offset is increased 14b by some predetermined value $\Delta O$, for example, some percentage of the first calibration offset, for example, 0.05 to 0.2% of the first calibration offset.

Subsequently, a new value of the first dew point is calculated using the new calibration offset for the measured relative humidity differing by $\Delta O$ from the previously used one. Subsequently, the procedure shown in FIG. 2 can be iterated until a constant value of the dew point within the predetermined range $\Delta\tau$ is determined. After a constant value of the dew point within the predetermined range $\Delta\tau$ is determined, the humidity sensor is well calibrated.

Figure 3:
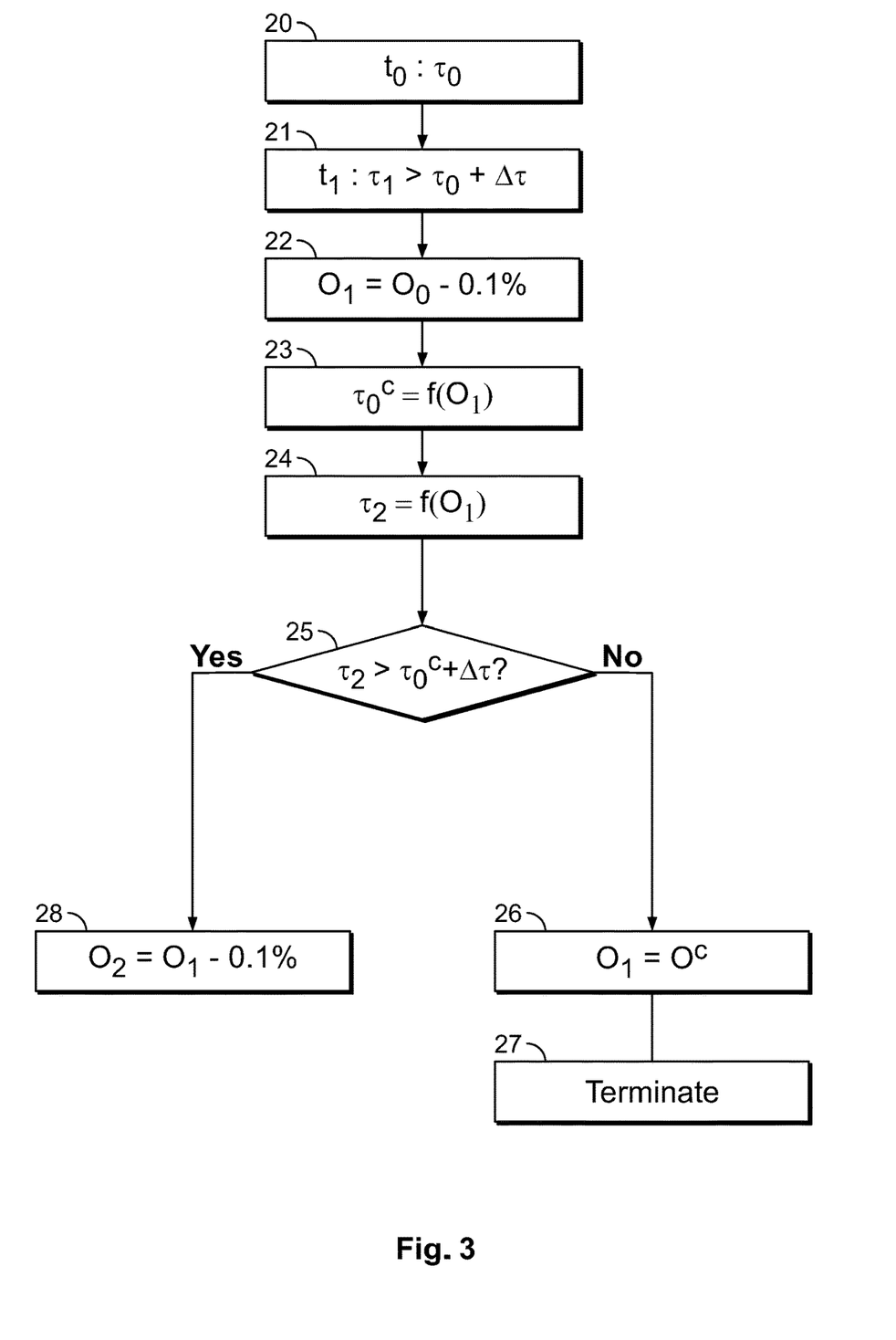
FIG. 3 represents another flow chart illustrating a calibration process according to a particular embodiment of the present invention.

FIG. 3 illustrates another concrete example of the inventive calibration procedure. At a time $t_0$ a dew point $\tau_0$ is determined 20 by the humidity sensor device that is to be calibrated in a closed environment at a temperature of $T_0$. The determination of the dew point $\tau_0$ is based on an initial calibration offset $O_0$ for the measured relative humidity. The temperature $T_0$ may be, for example, $\tau_0=24.7°$ C. The dew point $\tau_0$ is determined from a measured relative humidity $\varphi_0$. For example, $\tau_0=11.9°$ C. and $\varphi_0=44.8\%$.

After some time $t_1$ the dew point $\tau_1$ is determined 21 from a measured relative humidity $\varphi_1$. During the time period $t_1-t_0$ self-heating of the humidity sensor device results in a temperature increase of the local environment to a temperature $T_1 > T_0$. For example, $T_1=27.7°$ C., $T_1=12.8°$ C. and $\varphi_1=39.6\%$. In this example, the determined dew point $\tau_1$ has increased with respect to $\tau_0$ by more than some tolerance $\Delta\tau$, for example, $\Delta\tau=0.1°$ C. Thus, the relative humidity is measured too high, i.e., the calibration offset $O_0$ is too high. Consequently, the calibration offset is reduced by a predetermined amount $\Delta O$ to obtain a new calibration offset $O_1$ for the measured relative humidity 22, for example, $O_1=O_0-0.1\%$, if the predetermined amount $\Delta O$ is chosen to be 0.1%.

Using the new calibration offset $O_1$, the initially determined dew point is re-determined 23 to obtain a corrected value for the initial dew point: $\tau_0^c=f(O_1)$. Subsequently, using the new calibration offset $O_1$ a new value $\tau_2$ for the dew point is determined 24 at a time $t_2$. During the time period $t_2-t_1$ the self-heating of the humidity sensor device progressed such that the temperature of the local environment increased to $T_2 > T_1 > T_0$, for example, $T_2=28.1°$ C.

The new value $\tau_2$ for the dew point is compared with the corrected value for the initial dew point $\tau_0^c$ and if the values are the same within the predetermined tolerance $\Delta\tau$, it is determined that the new calibration offset $O_1$ for the measured relative humidity is the desired correct one 26 and the calibration process is terminated 27. If, on the other hand, $\tau_2 > \tau_0^c + \Delta\tau$, the calibration offset is further corrected $O_2=O_1-0.1\%$. The initially determined dew point is re-determined again to obtain a corrected value for the initial dew point using the corrected offset $O_2$: $\tau_0^c=f(O_2)$. Again, a new value of the dew point is determined after a time $t_3 > t_2$ and the above-described procedure is re-iterated until the determined respective new value for the dew point does not differ from the respective corrected new value for the initial dew point by more than the predetermined tolerance $\Delta\tau$. At the end of the iteration process the humidity sensor is well calibrated.

The procedures described above with reference to FIGS. 2 and 3 can, in principle, be applied to the problem of an initial calibration of a manufactured humidity sensor device or the problem of aging. During the aging of the humidity sensor device auto-recalibration can, thus, be performed in order to maintain correct operation of the already initially calibrated humidity sensor device over service time. In-field calibration can be useful for fine tuning after a first calibration that was performed under laboratory conditions. For example, auto-re-calibration can be performed at any start-up operation of the humidity sensor device installed in the field, for example, installed in an automobile. Auto-re-calibration can also be initiated on a regular periodic basis. For example, in periods of ten minutes ten measurements can be performed within one second, respectively, using the self-heating while increasing the processor load.

Figure 4:
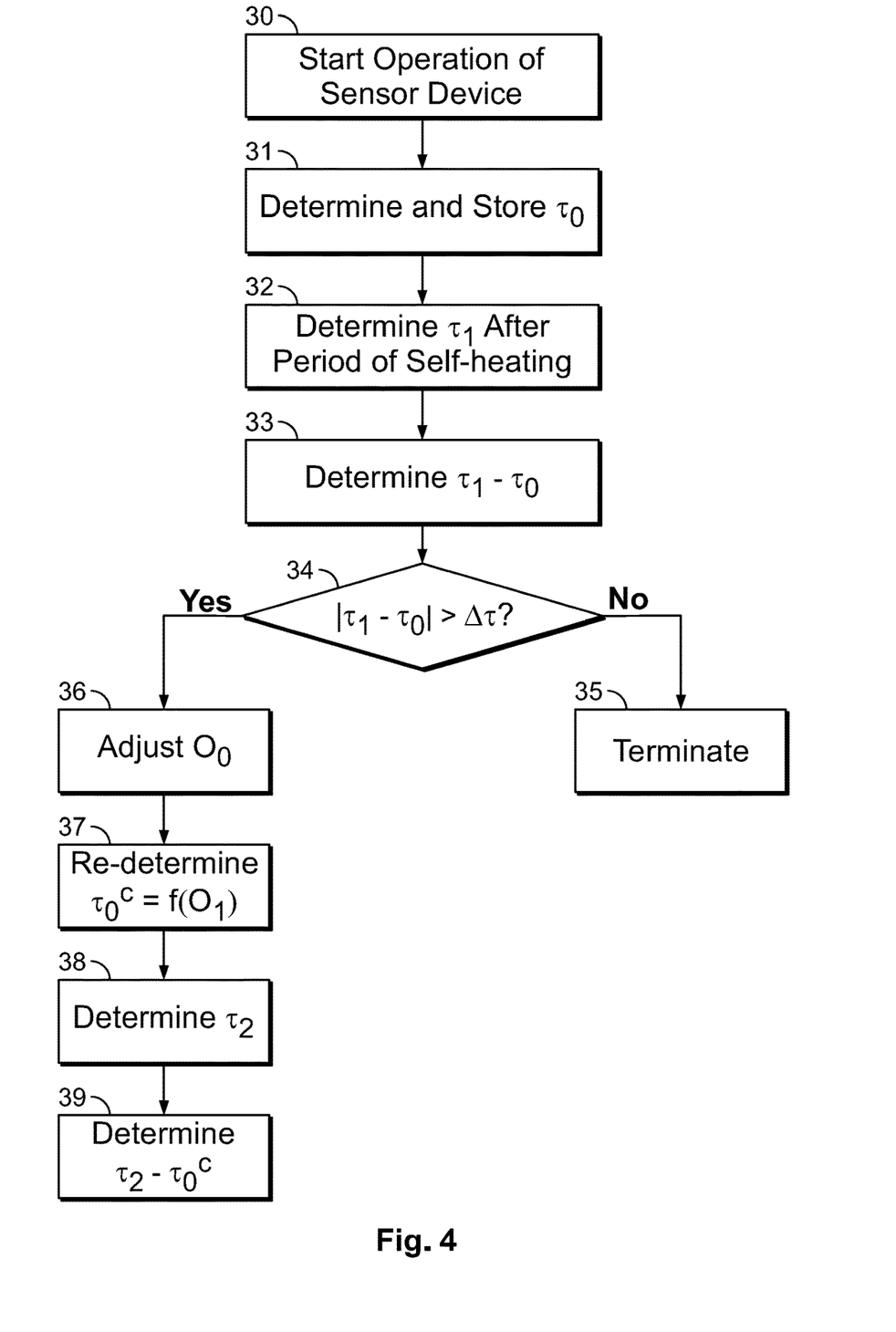
FIG. 4 represents another flow chart illustrating an auto-re-calibration process of an already initially calibrated and aging relative humidity sensor device.

FIG. 4 illustrates an auto-re-calibration process according to an example of the present invention. Operation of the humidity sensor device is started at step 30. Operation can be periodically started, for example, in time periods of hours or some 10 minutes. Immediately after start of the operation a dew point $\tau_0$ is determined by the humidity sensor device with an initial calibration offset $O_0$ of relative humidity based on measurement of a relative humidity $\varphi_0$ and stored 31 in a memory of the humidity sensor device.

After a predetermined time period of self-heating of the humidity sensor device, a new value $\tau_1$ of the dew point is determined 32 and the difference between the new value $\tau_1$ and the initial value $\tau_0$ is determined 33 by a processing means of the humidity sensor device. It is determined 34 whether or not the absolute value of the difference exceeds a predetermined tolerance $\Delta\tau$ of calibration error. If the predetermined tolerance $\Delta\tau$ is not exceeded, no adjustment of the calibration is needed, and the procedure is terminated 35. If the predetermined tolerance $\Delta\tau$ is exceeded, the initial calibration offset $O_0$ of relative humidity (set by an initial calibration process, for example, performed after manufacture of the humidity sensor device and before a first operation in the field) has to be adjusted 36. In this case, if $\tau_1 > \tau_0$, the initial offset $O_0$ is reduced by a predetermined amount $\Delta O$, and if $\tau_1 < \tau_0$, the initial offset $O_0$ is increased by the predetermined amount $\Delta O$, in order to obtain a corrected offset $O_1$.

Next, the initial value of the dew point is re-determined 37 using the adjusted offset $O_1$ in order to obtain a corrected initial dew point $\Delta_0{}^c$. In a further measurement/determination step 38 the dew point $\tau_2$ is determined after some predetermined time period and the difference between the newly determined dew point $\tau_2$ and the corrected initial dew point $\Delta_0{}^c$ is determined. Again, if the absolute value of the difference exceeds the predetermined tolerance $\Delta\tau$, the actual calibration offset $O_1$ is adjusted (increased or decreased depending on the sign of the difference) by the predetermined amount $\Delta O$ and the corrected initial dew point $\tau_0{}^c$ is re-determined using the newly corrected offset $O_2$. This procedure can be re-iterated (for example, with measurements every 100 ms) until the offset is adjusted such that a newly determined dew point does not differ from the actual corrected initial dew point by more than the predetermined tolerance. When the iteration process is completed the humidity sensor is well re-calibrated.

It is noted that in order to cope with the aging problem it is also possible to adjust the calibration slope. For example, a relative humidity sensor may be well calibrated for a relative humidity of 50% but erroneously calibrated at a relative humidity of 30%. Instead of correcting the offset at a relative humidity of 30% one may, alternatively, calculate the slope that leads to an accurate calibration at a relative humidity of 30% as well as 50%. The adjustment of the slope may be based on some linear or non-linear function. Adjusting the slope over the full range of 0% to 100% results in accurate re-calibration.

Figure 5:
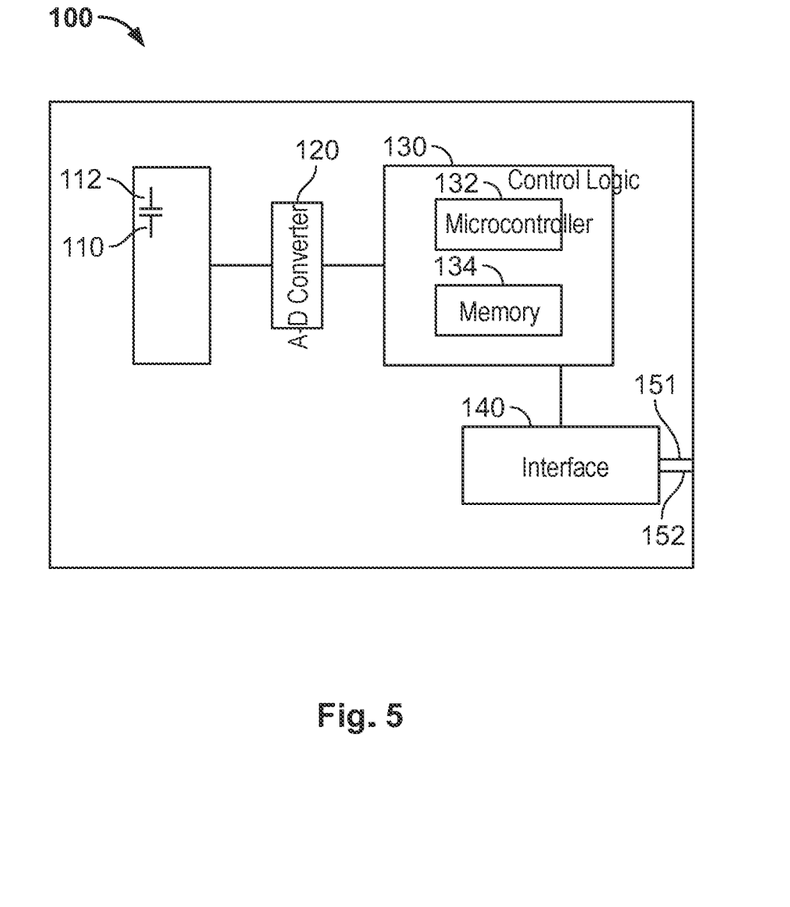
FIG. 5 represents a schematic diagram showing basic components of a humidity sensor device according to an embodiment of the present invention.

The procedures described above with reference to FIGS. 2 to 4 allow for a very efficient and reliable as well as a time-saving manner of calibrating a humidity sensor device both at an initial state before the first operation of the sensor and during the service time. The block diagram of FIG. 5 shows a configuration of a humidity sensor device 100 wherein the above-described procedures are implemented. The humidity sensor device 100 comprises a humidity sensing means 110 including a sensing capacitor 112 and configured for measuring a relative humidity.

The sensing capacitor 112 includes two parallel metal plates each having covering films with a polyimide dielectric layer serving as a capacitor dielectric. The absorption of moisture by the polyimide dielectric layer changes the dielectric constant of the capacitor. As such, by knowing a constant reference capacitance (established by a reference capacitor, for example), one may calculate a relative humidity by measuring the change in the capacitance of the sensing capacitor 112 because the capacitance changes with humidity of the ambient conditions.

The humidity sensing means 110 is connected to an analog-digital converter 120 for providing a control logic 130 with a digital data stream. The control logic 130 comprises a processing means 132, for example, a microcontroller, and a memory 134. Calibration data and data used for the calibration procedure can be stored in the memory 134. Moreover, the memory 134 stores a program product for carrying out the calibration procedure according to the above-described embodiments.

The control logic 130 is connected to an interface 140 for data output via data lines 151 and 152. The interface 140 can, for example, be an I²C interface with signal lines SDA and SCL. At least some of the components shown in FIG. 5 can be formed on a single microchip or printed circuit board.

All previously discussed embodiments are not intended as limitations but serve as examples illustrating features and advantages of the invention. It is to be understood that some or all of the above-described features can also be combined in different ways.

What is claimed is:

1. A method of calibrating a humidity sensor device comprising the steps of:
   a) determining, by the humidity sensor device using a first calibration offset, a first dew point and a first relative humidity at a first temperature in an environment;
   b) subsequently heating the humidity sensor device by self-heating, thereby heating the environment to a second temperature higher than the first temperature;
   e) subsequently determining a second dew point at the second temperature by the humidity sensor device;
   d) subsequently determining whether the determined second dew point differs from the determined first dew point by more than a predetermined difference;
   e) subsequently changing the first calibration offset of the humidity sensor device by a predetermined value to obtain a second calibration offset if it is determined that the determined second dew point differs from the determined first dew point by more than the predetermined difference;
   f) determining a new value of the first dew point based on the changed calibration offset:
   g) subsequently determining a third dew point at a third temperature by the humidity sensor device;
   h) subsequently determining whether the determined third dew point differs from the determined new value of the first dew point by more than the predetermined difference; and
   i) subsequently changing the calibration offset of the humidity sensor device by the predetermined value if it is determined that the determined third dew point differs from the determined new value of the first dew point by more than the predetermined difference.

2. The method according to claim 1, wherein the first and second calibration offsets are related to the relative humidity determined by the humidity sensor device; and
   i) the first calibration offset is increased by the predetermined value if it is determined that the second dew point is lower than the determined first dew point; and
   ii) the first calibration offset is decreased by the predetermined value if it is determined that the second dew point is higher than the determined first dew point.

3. The method according to claim 1, wherein the predetermined value is some predetermined fraction of the first calibration offset.

4. The method according to claim 1, further comprising repeating the steps f) to i) until the determined respective dew point determined in step g) differs from the determined respective new value of the first dew point determined in step f) by not more than the predetermined difference.

5. The method according to claim 1, wherein the third temperature differs from the second temperature by less than 10% of the second temperature.

6. The method according to claim 1, further comprising storing the first dew point, the determined first relative humidity and the first temperature in a memory of the humidity sensor device.

7. The method according to claim 1, wherein the heating of the humidity sensor device is a self-heating by means of a processing means of the humidity sensor device.

8. The method according to claim 1, wherein steps a) to i) are performed on a periodical basis with a time period of some hours or minutes.

9. An article of manufacture including a non-transitory, tangible computer readable storage medium having instructions stored thereon that, in response to execution by a processor, cause the processor to perform operations comprising the method according to claim 1.

10. A humidity sensor device, comprising a memory for storing the non-transitory, tangible computer readable storage medium according to claim 9 and a processor means configured to run the non-transitory, tangible computer readable storage medium according to claim 9.

11. A method of calibrating a humidity sensor device comprising:
   a) determining, by the humidity sensor device using a first calibration offset, a first dew point and a first relative humidity at a first temperature in an environment;
   b) subsequently heating the humidity sensor device by self-heating, thereby heating the environment to a second temperature higher than the first temperature;
   c) subsequently determining a second dew point at the second temperature by the humidity sensor device;
   d) subsequently determining whether the determined second dew point differs from the determined first dew point by more than a predetermined difference; and
   e) subsequently changing the first calibration offset of the humidity sensor device by a predetermined value to obtain a second calibration offset if it is determined that the determined second dew point differs from the determined first dew point by more than the predetermined difference, wherein the predetermined difference is in the range of 0.05° C. to 0.5° C.

12. The method according to claim 11, wherein steps a) to e) are performed on a periodical basis with a time period of some hours or minutes.

13. A method of calibrating a humidity sensor device comprising:
   a) determining, by the humidity sensor device using a first calibration offset, a first dew point and a first relative humidity at a first temperature in an environment;
   b) subsequently heating the humidity sensor device by self-heating, thereby heating the environment to a second temperature higher than the first temperature;
   c) subsequently determining a second dew point at the second temperature by the humidity sensor device;
   d) subsequently determining whether the determined second dew point differs from the determined first dew point by more than a predetermined difference; and
   e) subsequently changing the first calibration offset of the humidity sensor device by a predetermined value to obtain a second calibration offset if it is determined that the determined second dew point differs from the determined first dew point by more than the predetermined difference, wherein at least the steps a) to e) are performed automatically at a predetermined time period between 10 and 2 times an hour.

* * * * *